(12) United States Patent
Ward (10) Patent No.: US 9,032,812 B2
(45) Date of Patent: May 19, 2015

(54) METHOD AND SYSTEM FOR DETERMINING CREEP CAPABILITY OF TURBINE COMPONENTS PRIOR TO OPERATION

(75) Inventor: John David Ward, Woodruff, SC (US)

(73) Assignee: General Electric Company, Schenectady, NY (US)

( * ) Notice: Subject to any disclaimer, the term of this patent is extended or adjusted under 35 U.S.C. 154(b) by 373 days.

(21) Appl. No.: 13/490,191

(22) Filed: Jun. 6, 2012

(65) Prior Publication Data

US 2014/0060200 A1    Mar. 6, 2014

(51) Int. Cl.
| | |
|---|---|
| *G01L 1/22* | (2006.01) |
| *G01N 29/04* | (2006.01) |
| *G01N 3/08* | (2006.01) |
| *F01D 21/00* | (2006.01) |
| *F01D 21/12* | (2006.01) |
| *G01M 15/14* | (2006.01) |

(52) U.S. Cl.
CPC ................ *G01N 3/08* (2013.01); *F01D 21/003* (2013.01); *F01D 21/12* (2013.01); *G01M 15/14* (2013.01); *F05D 2260/81* (2013.01); *F05D 2260/83* (2013.01)

(58) Field of Classification Search
CPC ...... F01D 21/003; F01D 21/12; G01M 15/14; F05D 2260/81; F05D 2260/83; G01N 3/08
See application file for complete search history.

(56) References Cited

U.S. PATENT DOCUMENTS

| | | | |
|---|---|---|---|
| 8,006,544 B2 | 8/2011 | Holmes et al. | |
| 2004/0240600 A1 | 12/2004 | Freyer et al. | |
| 2009/0133381 A1 | 5/2009 | Holmes et al. | |

OTHER PUBLICATIONS

Search Report and Written Opinion from EP Application No. 13170607.9 dated Sep. 24, 2013.

*Primary Examiner* — Lisa Caputo
*Assistant Examiner* — Brandi N Hopkins
(74) *Attorney, Agent, or Firm* — Armstrong Teasdale LLP (57) ABSTRACT

A method and system for determining creep capability of turbine components is provided. A plurality of turbine components are manufactured from a material having known creep characteristics. Each of the plurality of turbine components is subjected to at least one of tensile stress, centrifugal stress and thermal stress, until a measurable amount of creep is acquired. The turbine components so tested are compared against known creep characteristics for the material used in the components. Components exhibiting an amount of creep greater than a predefined amount of creep will be separated from the plurality of turbine components and not placed into service.

20 Claims, 6 Drawing Sheets

METHOD AND SYSTEM FOR DETERMINING CREEP CAPABILITY OF TURBINE COMPONENTS PRIOR TO OPERATION

BACKGROUND OF THE INVENTION

This invention relates generally to a gas turbine engine, and, more specifically, to blades used within turbine engines.

Blades for gas turbine engines, during use, are subjected to substantial stresses caused by centrifugal force imposed on the blades by the rotation of the engine rotor. In addition, gas turbine engine blades are also subjected to extensive thermal cycling. As a result, such blades may be subject to creep at least along the lengthwise dimension of the blade, and possibly in other dimensions as well, which can lead to unacceptable changes in the blade dimensions and/or premature failure. Other engine components are also subject to creep from imposed forces and thermal cycling. Existing engine designs are created to accommodate a specified amount of creep in their components. The challenge is to determine when any particular component should be removed from service.

While it is presently believed to be impossible to completely eliminate creep, it would be desirable to develop a method of manufacture and testing of turbine blades that will enable the creep capability (the rate and conditions under which creep will occur) of a given turbine blade design to be determined.

BRIEF DESCRIPTION OF THE INVENTION

In one aspect, a method for determining creep capability of turbine components is provided. The method includes providing a plurality of turbine components fabricated from a material having known creep characteristics. The method further includes subjecting each of the plurality of turbine components to at least one of centrifugal stress, tensile stress, and thermal stress until a measurable amount of creep is induced in the turbine component. The method further includes measuring the amount of creep induced in each of the plurality of turbine components. The method still further includes determining the accumulation rate for each of the plurality of turbine components. The method still further includes comparing one of the measured amount of creep induced in each of the plurality of turbine components and the accumulation rate for each of the plurality of turbine components to a pre-defined tolerance value. The method further includes identifying turbine components having measured amounts of induced creep exceeding the pre-defined tolerance value. The method further includes segregating from the plurality of turbine components those turbine components identified as having measured amounts of induced creep that exceed the pre-defined tolerance value.

In still another aspect, a system for determining creep capability of turbine components is provided. The system includes a plurality of turbine components. The system further includes a test rig, configured to receive the plurality of turbine components; and a measurement apparatus. The system is configured to receive a plurality of turbine components fabricated from a material having known creep characteristics. The system is further configured to subject each of the plurality of turbine components to at least one of centrifugal stress, tensile stress, and thermal stress until a measurable amount of creep is induced in the turbine component. The system is further configured to measure the amount of creep induced in each of the plurality of turbine components. The system is further configured to determine the accumulation rate for each of the plurality of turbine components. The system is further configured to compare one of the measured amount of creep induced in each of the plurality of turbine components and the accumulation rate for each of the plurality of turbine components to a pre-defined tolerance value. The system is still further configured to identify turbine components having measured amounts of induced creep exceeding the pre-defined tolerance value. The system is still further configured to segregate from the plurality of turbine components, those turbine components identified as having measured amounts of induced creep that exceed the pre-defined tolerance value.

DETAILED DESCRIPTION OF THE INVENTION

As used herein, the terms "axial" and "axially" refer to directions and orientations extending substantially parallel to a longitudinal axis of a gas turbine engine. Moreover, the terms "radial" and "radially" refer to directions and orientations extending substantially perpendicular to the longitudinal axis of the gas turbine engine.

Figure 1:
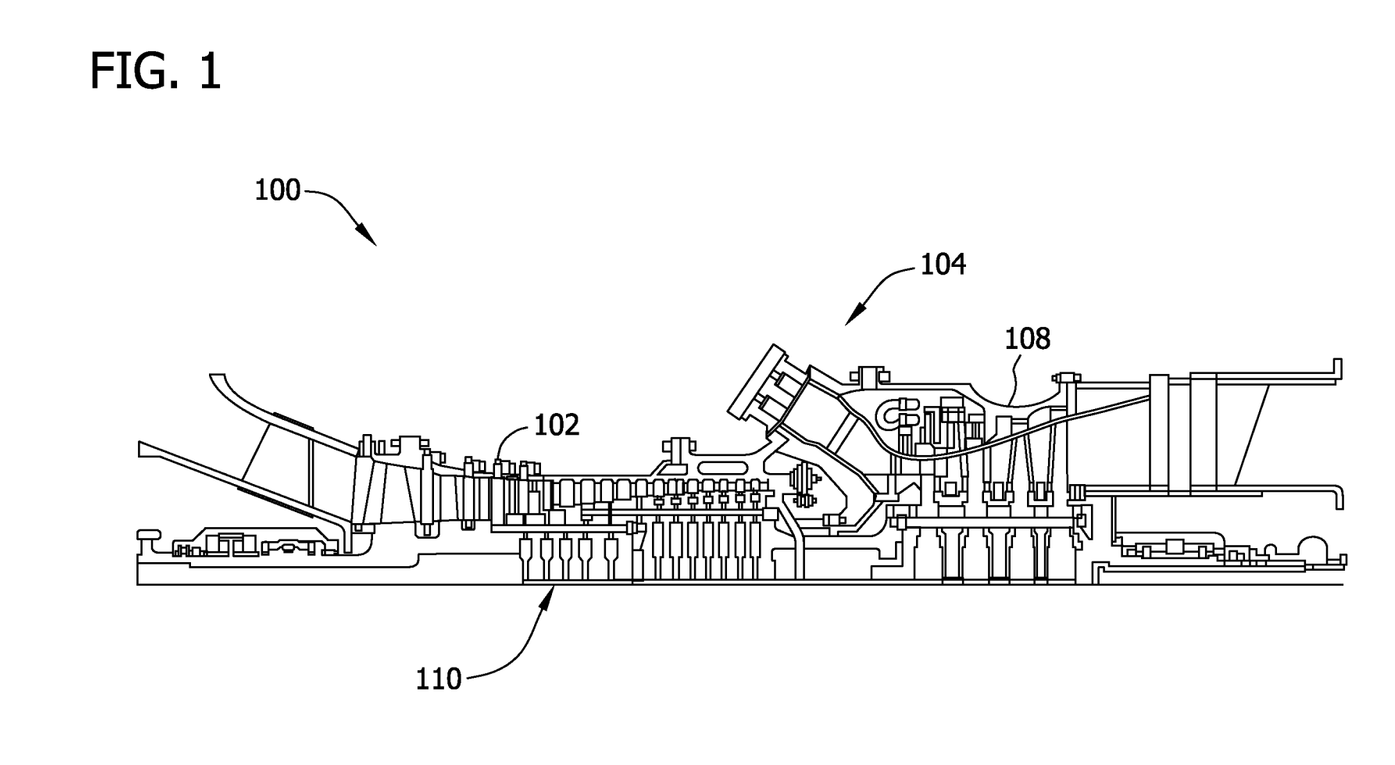
FIG. 1 is a schematic view of an exemplary gas turbine engine.

FIG. 1 is a schematic illustration of an exemplary gas turbine engine 100. Engine 100 includes a compressor assembly 102 and a combustor assembly 104. Engine 100 also includes a turbine 108 and a common compressor/turbine shaft 110 (sometimes referred to as a rotor 110).

In operation, air flows through compressor assembly 102 such that compressed air is supplied to combustor assembly 104. Fuel is channeled to a combustion region and/or zone (not shown) that is defined within combustor assembly 104 wherein the fuel is mixed with the air and ignited. Combustion gases generated are channeled to turbine 108 wherein gas stream thermal energy is converted to mechanical rotational energy. Turbine 108 is rotatably coupled to shaft 110. It should also be appreciated that the term "fluid" as used herein includes any medium or material that flows, including, but not limited to, gas and air.

Figure 2:
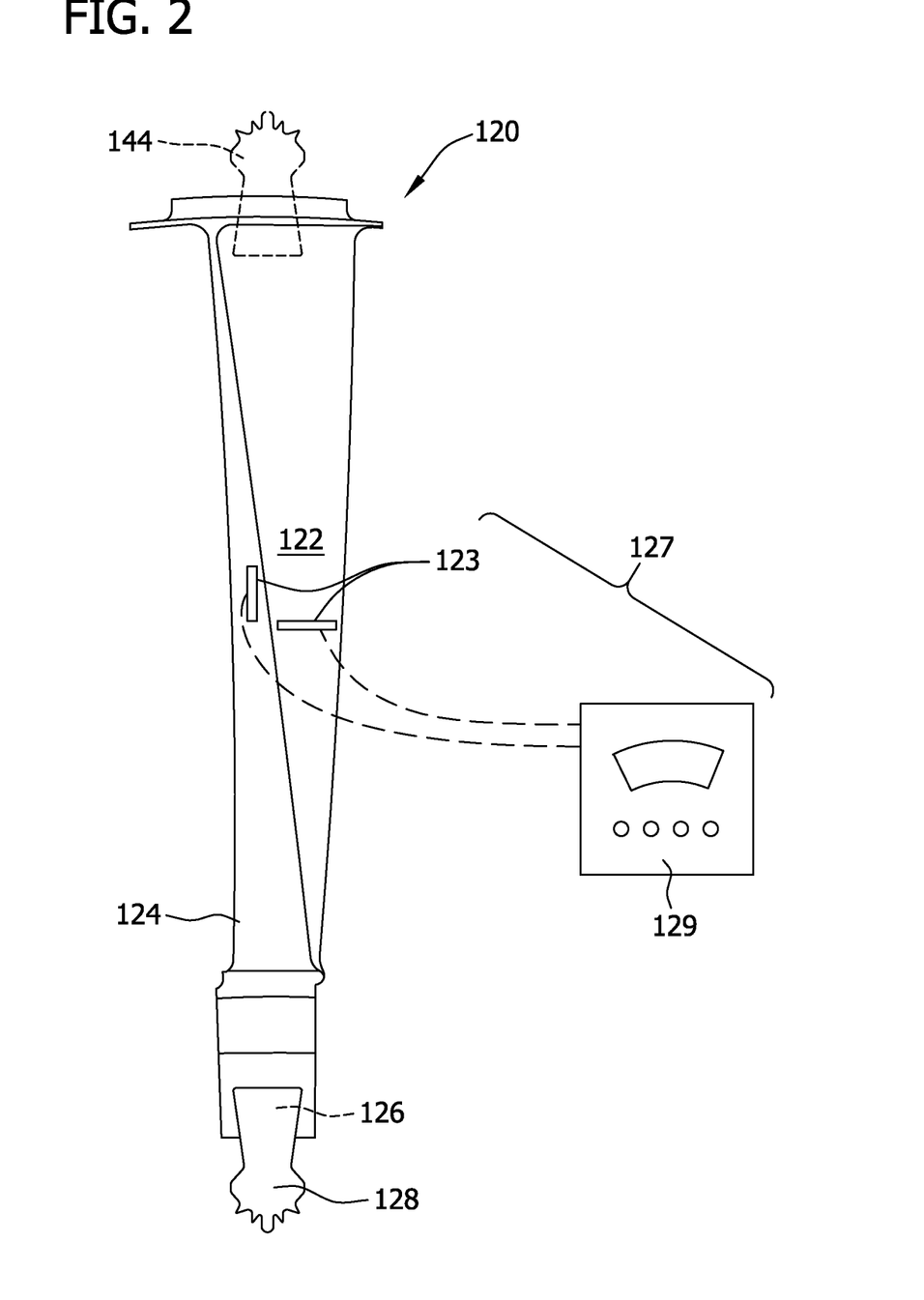
FIG. 2 is a simplified end view of an exemplary gas turbine blade.

FIG. 2 is simplified axial view of a typical gas turbine blade 120. Blade 120 includes airfoil portion 122, root 124, shank 126 and dovetail 128, for connecting blade 120 to a turbine rotor (not shown). While dovetail 128 is illustrated as having an axial-entry type dovetail construction, it is understood that the present disclosure is equally applicable to blades having tangential-entry type dovetail constructions, or other mechanisms for attachment to an engine rotor.

Figure 3:
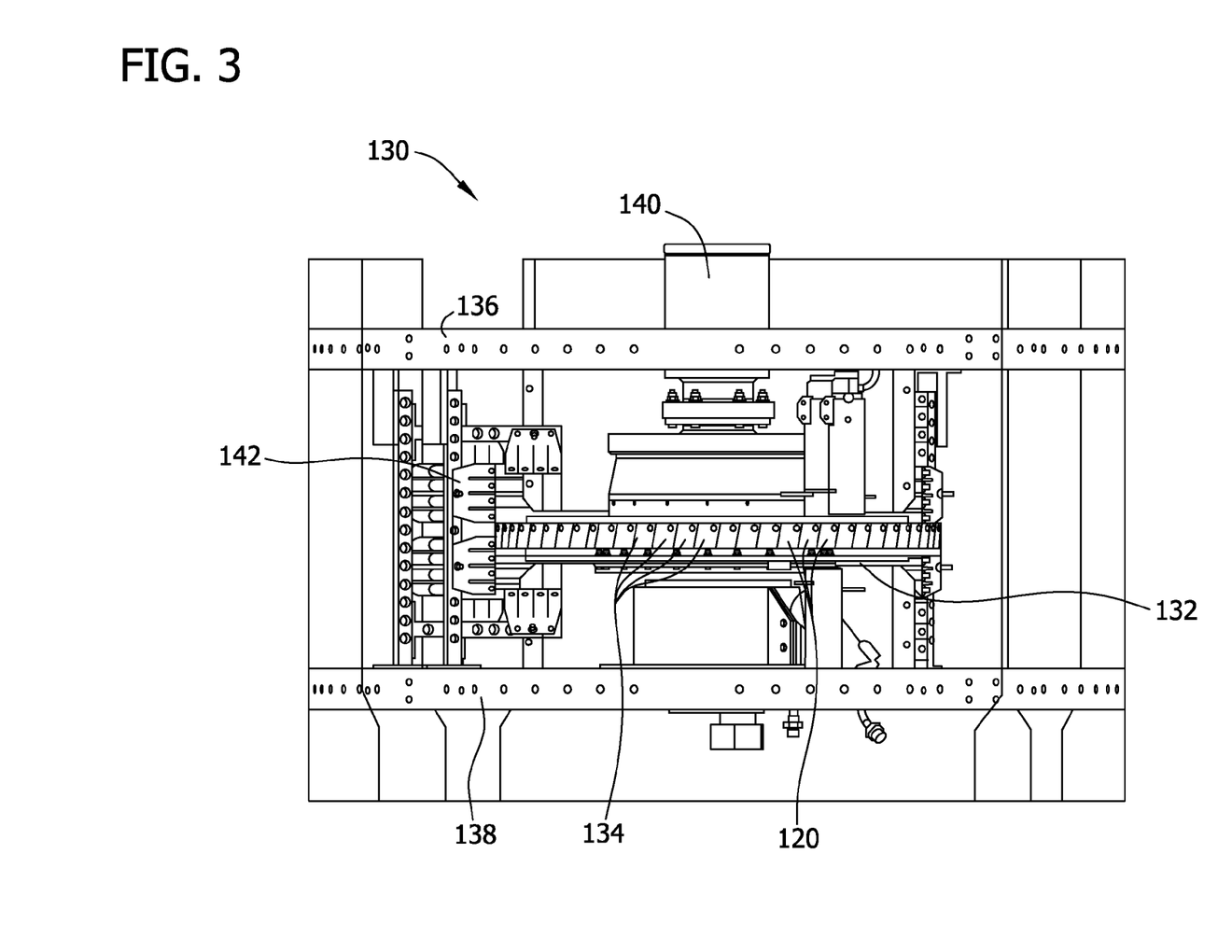
FIG. 3 is a side elevation of an exemplary hot spin test rig for testing gas turbine blades.

FIG. 3 is a schematic illustration of a portion of a turbine blade hot test spin rig 130. In an exemplary embodiment, turbine blades 120 are placed into spin test rig 130, for spin stress testing under controlled temperature conditions. Spin rig 130 includes disk 132, which includes a plurality of fixed or removable dummy blades 134 for balance. Several slots will be open, into which blades 120 are inserted, and removed after being subjected to spin tests. Hot test spin rig 130 also includes top plate 136 and bottom plate 138, as shields in case of failure of one of dummy blades 134 or test blades 120. Disk 132 is driven by drive shaft 140. One or more heating elements 142 are positioned to surround the tips of dummy blades 134 and blades 120.

Heating of blades 120 may be accomplished by any suitable means, such as radiative, inductive, or conductive heating, or by grossly heating the entire test chamber, such as by convective heating.

Figure 6:
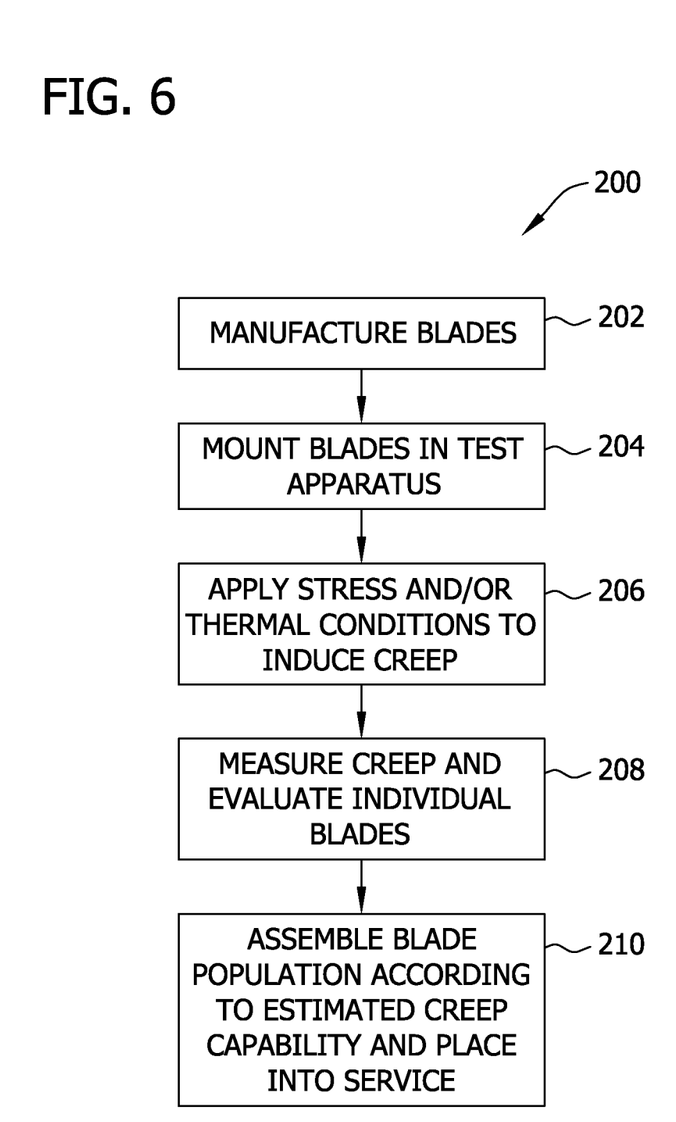
FIG. 6 is a flow chart illustrating an exemplary method for determining creep capability in turbine components.

FIG. 6 is a flow chart illustrating an exemplary method 200 for determining creep capability in turbine components. In the exemplary embodiment, a plurality of blades 120 is manufactured 202 to a sufficient state of completion to enable mounting and testing in test rig 130. Alternatively, each blade may be mounted to test rig 130, using clamping structures 302, 304, as described herein with respect to FIG. 7. Each blade 120 has known dimensions, prior to testing. Each blade 120 is provided with a dovetail 128 or other permanent or non-permanent feature that permits blade 120 to be affixed to rig 130. Blades 120 are mounted 204 in rig 130. Once blades 120 are mounted in rig 130, centrifugal stress and thermal loads are applied 206 to blades 120 for a sufficient time until blades 120 acquire measurable creep or elongation in one or more directions, e.g., relative to a longitudinal axis L (shown in FIG. 2) of each blade 120.

Measurement 208 of acquired creep is accomplished using any suitable measurement equipment 127, including, for example, suitably placed strain gauges 123 connected to suitably configured instrumentation 129. Measurement equipment 127 may be configured to measure acquired creep in real time during a test run, or may be connected periodically during and/or after the test, as desired. In another exemplary embodiment, measurement 208 of acquired creep is accomplished by removing the blade 120 from testing rig 130, and subjecting blade 120 to testing, e.g., by a coordinate measurement machine, using touch probes, to physically measure the tested blade and compare the post-test measurements to the known pre-test measurements. An estimated future creep rate or capability (also known as "accumulation rate") is then calculated, based on the amount of acquired creep and the number of revolutions, rotational speed of the spin test rig, the temperatures used, the number of thermal cycles, etc., using known methods for calculating creep.

The measured acquired creep and/or corresponding calculated accumulation rate are then correlated to the known creep rate of the material from which the blades are manufactured. For each blade, or other component type, and material, tolerance values, for post-test measured creep and calculated accumulation rate, will be established. The creep tolerance value will be a maximum value of creep that a blade will be permitted to acquire during testing, for that blade to be allowed to enter into service. The accumulation rate tolerance value will be the corresponding accumulation rate, calculated based on the amount of creep acquired during testing, that a blade 120 will be permitted to have and still be allowed to enter into service. The creep tolerance value and accumulation rate tolerance value correspond to a predefined desired service life (and maximum amount of creep permitted during that service life) for a turbine blade or other turbine component. Accordingly, when a component has been subjected to service conditions that would correspond to the previously-defined service life and maximum amount of creep permitted, the component is removed from service.

The greater the amount of measured creep after testing, the greater the accumulation rate is, and the greater the likelihood that the component will fail sooner rather than later. Such "fast creeping" blades will be closer to failure, or to a pre-defined amount of creep that is deemed to be unacceptable for use in service.

Accordingly, each blade 120 that undergoes testing in rig 130 will have a measurable amount of creep. Knowing the creep rate of the material from which each blade 120 is manufactured, the estimated remaining amount of creep available in each blade is calculated 208. Those blades 120 having a measured amount of acquired creep and corresponding calculated accumulation rate, that exceed the aforementioned creep and accumulation tolerance values will be segregated from a manufactured lot. The remaining blades 120 are assembled 210 into a population to be placed into service. Each of blades 120 from that population is then withdrawn from service after a pre-defined number of hours of use, so that each blade 120 is withdrawn before it can reach or pass its safe and useful service life. The segregated blades 120 or other components may be sold or otherwise distributed as "shortened service life" components, destroyed, or otherwise suitably disposed of.

Whether blades 120 are placed in a population of full service life components, or shortened life components, each blade will have a predetermined estimated service life expectancy. Such blades may be put into service for a period of time, and removed at or before the end of their respective service life expectancies, using any suitable margin of error.

Figure 4:
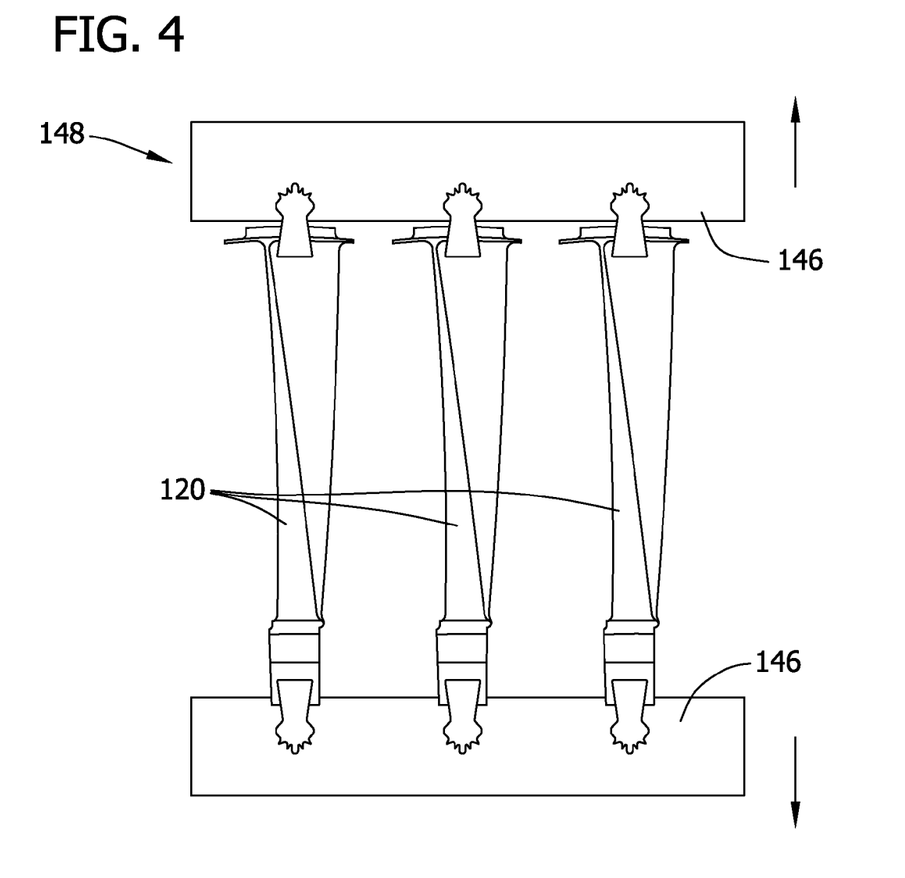
FIG. 4 is a schematic illustration of a top view of an alternative blade testing arrangement.
Figure 5:
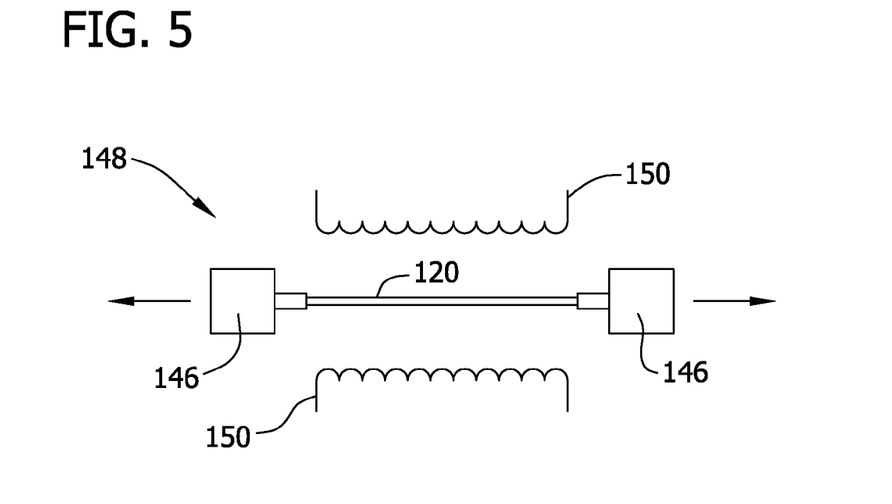
FIG. 5 is a side elevation of the alternative blade testing arrangement of FIG. 4.

In an alternative exemplary embodiment, blades 120 are tested through application of direct tension and/or thermal stress, in a manner similar to that previously described with respect to the spin test rig 130 embodiment of FIG. 3. FIG. 4 is a schematic illustration of an alternative testing rig 146, and FIG. 5 is a side elevation of the same alternative testing rig 146. In an alternative exemplary embodiment, blades 120 are provided with a second dovetail fitting 144 at their tips (shown in FIG. 2 in broken lines). Having second opposing dovetail fittings 144 enables blades 120 to be fitted to opposed mounting brackets 146 of a stationary tensile testing rig 148. Heating elements 150 are provided to enable blades 120 to be put through thermal cycles as desired. Once fitted into rig 148, blades 120 will be subjected to tensile and thermal stress loading until a small but measurable amount of creep has been induced into each blade 120.

As described above with respect to the exemplary embodiment of FIG. 3, blades 120 that have been subjected to testing in tensile testing rig 148 are then measured, and separated according to whether the measured amount of induced creep in each blade corresponds to an acceptable or unacceptable creep capability. Those blades 120 found to have an unacceptable creep capability are segregated and not placed into service, as described above.

Figure 7:
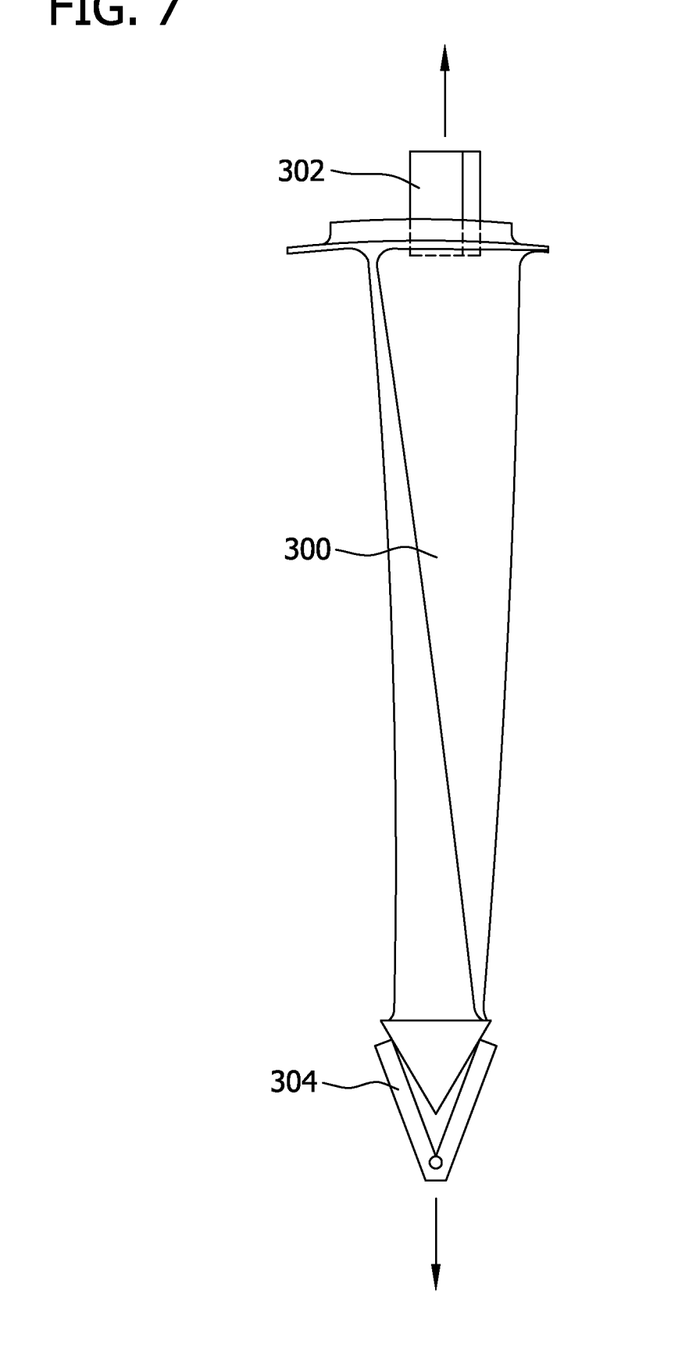
FIG. 7 is a simplified schematic illustration of an exemplary component with clamping structures for use with a testing arrangement.

In another exemplary embodiment, turbine components may not incorporate permanent mounting structures (such as dovetails), or may not have the capacity for having temporary mounting structures fabricated into them, to facilitate their being mounted into a test rig. Such components may be tested according to the methods and systems described herein through the employment of suitably configured clamping structures releasably affixed to appropriate locations on the parts to be tested. FIG. 7 is a simplified schematic illustration of an exemplary component 300 with clamping structures 302, 304 for use with a testing arrangement. Clamping structures 302, 304, in turn, may be permanently- or removably-affixed to the spin- or tensile-testing equipment (not shown in FIG. 7).

While the embodiments of FIGS. 3 and 4 are described in the context of testing turbine blades to determine their creep capability, other turbine components may likewise be tested for creep capability, such as combustion components, static hot gas path hardware, and other creep-limited hardware . . . .

The invention described herein provides several advantages over known methods of manufacture and placement into service, of turbine components. For example, one advantage is that the blades or other components are placed into service with a more precise and detailed knowledge of the expected useful service life of the components. Once the creep capability of each production blade has been determined, as described above, those blades that have been determined to have an accelerated creep capability will be culled from a batch of blades that have been tested, and not put into service. Using this method can potentially eliminate or reduce the need for other types of creep management, such as periodic measurement of blades in service, e.g., through the use of a Coordinate Measuring Machine ("CMM") or periodic treatment of the blades, such as through heat treatments to alter the microstructure of the blade material.

Exemplary embodiments of a method and a system for determining creep capability of turbine components are described above in detail. The method and system are not limited to the specific embodiments described herein, but rather, components of systems and/or steps of the methods may be utilized independently and separately from other components and/or steps described herein. For example, the method may also be used in combination with other turbine component production and quality control systems and methods, and are not limited to practice with only the turbine blades as described herein. Rather, the exemplary embodiment can be implemented and utilized in connection with many other turbine applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the invention has been described in terms of various specific embodiments, those skilled in the art will recognize that the invention can be practiced with modification within the spirit and scope of the claims.

What is claimed is:

1. A method for determining creep capability of turbine components, comprising:
   coupling a plurality of turbine components to a spin test rig, wherein the plurality of turbine components are fabricated from a material having known creep characteristics;
   subjecting each of the plurality of turbine components to centrifugal stress and thermal stress in the spin test rig until a measurable amount of creep is induced in the turbine component;
   measuring the amount of creep induced in each of the plurality of turbine components;
   determining the accumulation rate for each of the plurality of turbine components;
   comparing one of the measured amount of creep induced in each of the plurality of turbine components and the accumulation rate for each of the plurality of turbine components to a pre-defined tolerance value; and
   placing into service only those turbine components identified as having measured amounts of induced creep that do not exceed the pre-defined tolerance value.

2. A method for determining creep capability of turbine components according to claim 1, wherein the turbine components are turbine blades.

3. A method for determining creep capability of turbine components according to claim 1, wherein subjecting each of the plurality of turbine components to thermal stress comprises:
   heating the turbine components, using one of radiative heating, inductive heating, conductive heating, convective heating.

4. A method for determining creep capability of turbine components according to claim 1, further comprising:
   establishing an expected average service life for the turbine components placed into service;
   determining whether the turbine components are meeting the previously-established expected average service life; and
   lowering the pre-defined tolerance value to increase the number of turbine components removed from eligibility for service, if the turbine components are determined not to be meeting the previously-established expected average service life.

5. A method for determining creep capability of turbine components, the method comprising:
   providing a plurality of turbine components fabricated from a material having known creep characteristics;
   providing a test rig for subjecting the plurality of turbine components to stresses;
   providing clamping structures configured to cooperate with the test rig and releasably retain the turbine components within the test rig;
   subjecting each of the plurality of turbine components to at least one of centrifugal stress, tensile stress, and thermal stress until a measurable amount of creep is induced in the turbine component;
   measuring the amount of creep induced in each of the plurality of turbine components;
   determining the accumulation rate for each of the plurality of turbine components;
   comparing one of the measured amount of creep induced in each of the plurality of turbine components and the accumulation rate for each of the plurality of turbine components to a pre-defined tolerance value;
   identifying turbine components having measured amounts of induced creep exceeding the pre-defined tolerance value; and
   segregating from the plurality of turbine components those turbine components identified as having measured amounts of induced creep that exceed the pre-defined tolerance value.

6. A method for determining creep capability of turbine components according to claim 5, comprising:

placing into service remaining ones of the plurality of turbine components not having been identified as having measured amounts of induced creep that exceed the pre-defined tolerance value.

7. A method for determining creep capability of turbine components according to claim 5, wherein subjecting each of the plurality of turbine components to at least one of centrifugal stress, tensile stress, and thermal stress until a measurable amount of creep is induced in the turbine component comprises one of:
 placing the turbine components into a spin test rig and subjecting the turbine components to centrifugal stresses, and
 placing the turbine components into a direct tensile loading test rig and subjecting the turbine components to tensile stresses.

8. A method for determining creep capability of turbine components according to claim 7, wherein subjecting each of the plurality of turbine components to at least one of centrifugal stress, tensile stress, and thermal stress until a measurable amount of creep is induced in the turbine component further comprises:
 subjecting the turbine components to thermal cycling.

9. A method for determining creep capability of turbine components according to claim 8, wherein subjecting the turbine components to thermal cycling comprises:
 heating the turbine components, using one of radiative heating, inductive heating, conductive heating, convective heating.

10. A method for determining creep capability of turbine components according to claim 5, wherein providing clamping structures comprises:
 providing mounting structures on opposed ends of the turbine components, to facilitate placement of the turbine components on a tension testing rig.

11. A system for determining creep capability of a turbine component, comprising:
 a test rig configured to receive a plurality of turbine components fabricated from a material having known creep characteristics;
 a plurality of heating elements positioned to be proximate the turbine components in the test rig; and
 a measurement apparatus; wherein the system is configured to:
 subject each of the plurality of turbine components to at least one of centrifugal stress, tensile stress, and thermal stress until a measurable amount of creep is induced in the turbine component;
 measure the amount of creep induced in each of the plurality of turbine components;
 determine the accumulation rate for each of the plurality of turbine components;
 compare one of the measured amount of creep induced in each of the plurality of turbine components and the accumulation rate for each of the plurality of turbine components to a pre-defined tolerance value; and
 place into service only those turbine components identified as having measured amounts of induced creep that do not exceed the pre-defined tolerance value.

12. A system for determining creep capability of turbine components according to claim 11, further configured to:
 segregate from the plurality of turbine components those turbine components identified as having measured amounts of induced creep that exceed the pre-defined tolerance value.

13. A system for determining creep capability of turbine components according to claim 11, wherein the turbine components are turbine blades.

14. A system for determining creep capability of turbine components according to claim 11, wherein the test rig comprises one of:
 a spin test rig configured to subject the turbine components to centrifugal stresses, and
 a direct tensile loading test rig configured to subject the turbine components to tensile stresses.

15. A system for determining creep capability of turbine components according to claim 14, wherein the plurality of heating elements is configured to subject the turbine components to thermal cycling.

16. A system for determining creep capability of turbine components according to claim 15, wherein the plurality of heating elements is configured to heat the turbine components, using one of radiative heating, inductive heating, conductive heating, convective heating.

17. A system for determining creep capability of turbine components according to claim 11, wherein
 the plurality of heating elements is configured to heat the turbine components, using one of radiative heating, inductive heating, conductive heating, convective heating.

18. A system for determining creep capability of turbine components, according to claim 11, further comprising:
 mounting structures configured to couple to opposed ends of the turbine components, to facilitate placement of the turbine components on a tension testing rig.

19. A system for determining creep capability of turbine components according to claim 11, further comprising:
 clamping structures configured to cooperate with the test rig and releasably retain turbine components within the test rig.

20. A system for determining creep capability of turbine components according to claim 11, further configured to:
 establish an expected average service life for the turbine components placed into service;
 determine whether the turbine components are meeting the previously-established expected average service life; and
 lower the pre-defined tolerance value to increase the number of turbine components removed from eligibility for service, if the turbine components are determined not to be meeting the previously-established expected average service life.

* * * * *